United States Patent
Alkhamis

(10) Patent No.: US 9,675,496 B1
(45) Date of Patent: Jun. 13, 2017

(54) DIAPER CHANGE ALERT

(71) Applicant: Zainab Alkhamis, Buffalo, NY (US)

(72) Inventor: Zainab Alkhamis, Buffalo, NY (US)

( * ) Notice: Subject to any disclaimer, the term of this patent is extended or adjusted under 35 U.S.C. 154(b) by 0 days.

(21) Appl. No.: 15/188,136

(22) Filed: Jun. 21, 2016

(51) Int. Cl.
*G01W 1/00* (2006.01)
*A61F 13/42* (2006.01)
*A61B 5/00* (2006.01)

(52) U.S. Cl.
CPC .............. *A61F 13/42* (2013.01); *A61B 5/445* (2013.01); *A61B 5/746* (2013.01); *A61F 2013/424* (2013.01)

(58) Field of Classification Search
CPC .... A61F 13/42; A61F 2013/424; A61B 5/445; A61B 5/746
USPC ................................................. 340/604, 573.5
See application file for complete search history.

(56) References Cited

U.S. PATENT DOCUMENTS

| | | | | |
|---|---|---|---|---|
| 4,851,816 A * | 7/1989 | Macias | .................. | A61B 5/113 128/204.23 |
| 5,264,830 A * | 11/1993 | Kline | ...................... | A61F 13/42 128/886 |
| 5,266,928 A * | 11/1993 | Johnson | .................. | A61F 13/42 128/886 |
| 5,392,032 A * | 2/1995 | Kline | ...................... | A61F 13/42 128/886 |
| 5,469,145 A * | 11/1995 | Johnson | .................. | A61F 13/42 128/886 |
| 5,838,240 A * | 11/1998 | Johnson | .................. | A61F 13/42 128/886 |
| 7,145,053 B1 * | 12/2006 | Emenike | .................. | A61F 13/42 200/61.02 |
| 2004/0220538 A1 * | 11/2004 | Panopoulos | ............ | A61F 13/42 604/361 |
| 2005/0079637 A1 * | 4/2005 | Wilhelm | .................. | A61F 13/42 436/518 |

(Continued)

FOREIGN PATENT DOCUMENTS

EP 1 187 585 B1 4/2006

OTHER PUBLICATIONS

Mohamed Y. E. Simik, et al., "A Design of Smart Diaper Wet Detector Using Wireless and Computer", Proceedings of The World Congress on Engineering and Computer Science, vol. II, Oct. 21-23, 2015, 5 pages.

(Continued)

*Primary Examiner* — Ojiako Nwugo
(74) *Attorney, Agent, or Firm* — Oblon, McClelland, Maier & Neustadt, L.L.P.

(57) ABSTRACT

A diaper change alert system, method, and computer-readable medium a diaper with wetness detection circuit installed inside a seat portion of the diaper, an ionic composition sensor installed inside the seat portion of the diaper, a humidity sensor installed inside the seat portion of the diaper, processing circuitry. The processing circuitry is configured to compute number of waste cycles per diaper change based on a signal received from the wetness detection circuit, compute a total time per diaper change based on a signal received from the wetness detection circuit, compute a rash threshold using rash information, receive sensor data, determine whether the rash threshold is reached, and transmit, via a network, a diaper change alert to an external device.

20 Claims, 7 Drawing Sheets

(56) References Cited

U.S. PATENT DOCUMENTS

| | | | |
|---|---|---|---|
| 2008/0074274 A1* | 3/2008 | Hu | A61F 13/42 340/573.5 |
| 2008/0208151 A1* | 8/2008 | Zacharias | A61F 13/42 604/361 |
| 2011/0263952 A1 | 10/2011 | Bergman et al. | |
| 2014/0266735 A1* | 9/2014 | Riggio | G08B 21/0205 340/573.5 |
| 2015/0148762 A1 | 5/2015 | Johnson et al. | |
| 2015/0282993 A1 | 10/2015 | Lin | |

OTHER PUBLICATIONS

"Help elderly and babies with diaper water sensors" http://www.examiner.com/article/help-elderly-and-babies-with-diaper-water-sensors, Feb. 7, 2014, 3 pages.

* cited by examiner

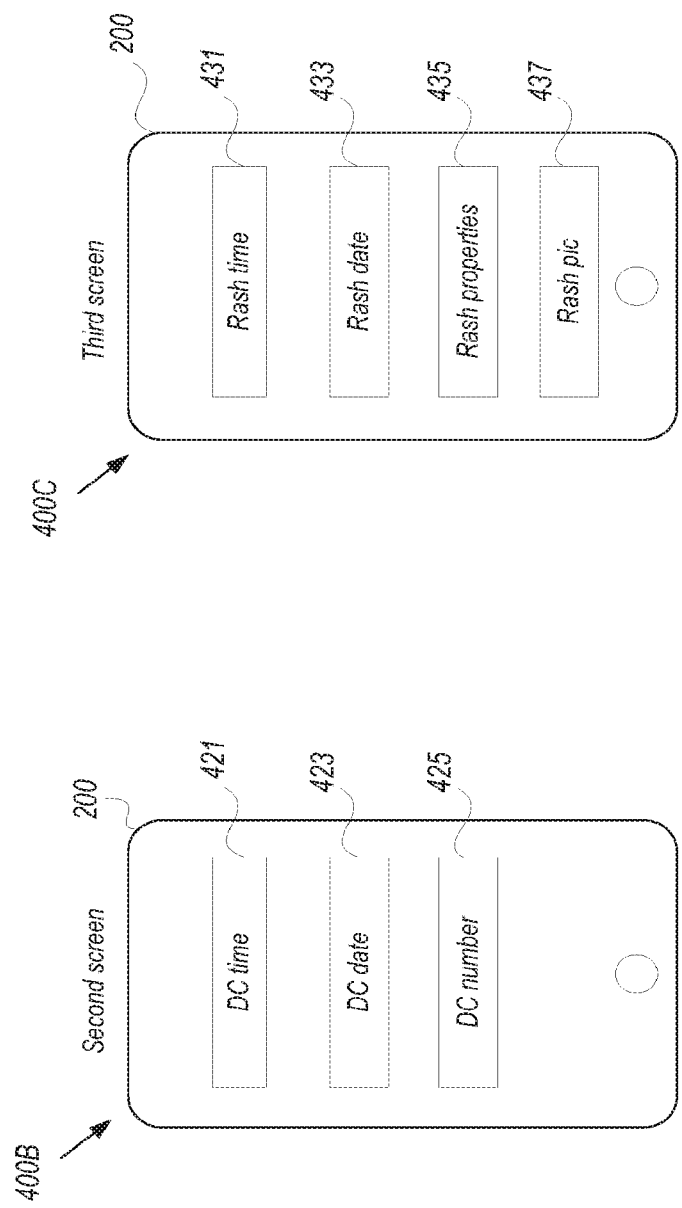

DIAPER CHANGE ALERT

GRANT OF NON-EXCLUSIVE RIGHT

This application was prepared with financial support from the Saudi Arabian Cultural Mission, and in consideration therefore the present inventor(s) has granted The Kingdom of Saudi Arabia a non-exclusive right to practice the present invention.

BACKGROUND

Field of the Disclosure

This application relates generally to improvements in a diaper and a diaper change alert application. More particularly, a diaper embedded with sensors and a diaper change alert application configured to send alerts to change a diaper before a rash occurs.

Description of the Related Art

Diapers or nappies help control infants waste in a relatively, clean, and healthy way. There are several types of diapers such as, disposable diapers and cloth that can be used for a child, adults and even animals. The purpose of a diaper is to absorb moisture and contain mess, so that the wearer can remain dry and comfortable after wetting or soiling themselves.

However, diapers have one major drawback; they can cause a skin rash. Skin rash can develop when the skin is exposed to wetness for a prolonged period of time, or if the skin is not exposed to air for prolonged increments of time. Diapers cause skin rash which develops when the skin is exposed to wetness for a long period of time, increased skin pH caused by urine and feces, and resulting breakdown of the stratum corneum, or outermost layer of the skin.

As such, a baby's diapers are often changed periodically or according to a pre-established timetable. Similar diaper change schedule can be established for adults or animals. Although such diaper change schedules are helpful, no prescribed time table can anticipate an individual wearer's changing physical condition. For example, a baby may urinate right after changing the diaper, which may go unnoticed for a prolonged period.

Hence, there remains a continuing need to provide improved diapers and alert systems that can manage the diaper change schedule according to more realistic changes in physical condition, thus reducing a probability of getting a skin rash.

SUMMARY

According to an embodiment of the present disclosure, there is provided a diaper change alert system. The system includes a diaper with wetness detection circuit installed inside a seat portion of the diaper, an ionic composition sensor installed inside the seat portion of the diaper, a humidity sensor installed inside the seat portion of the diaper, and processing circuitry. The processing circuitry is configured to compute number of waste cycles per diaper change based on a signal received from the wetness detection circuit, compute a total time per diaper change based on a signal received from the wetness detection circuit, compute a rash threshold using rash information, receive sensor data, determine whether the rash threshold is reached, and transmit, via a network, a diaper change alert to an external device.

Further, according to an embodiment of the present disclosure, there is provided a diaper change alert method. The method includes computing, using processing circuitry, number of waste cycles per diaper change, computing, using the processing circuitry, a total time per diaper change, computing, using the processing circuitry, a diaper change threshold using rash information, receiving, using the processing circuitry, sensor data. Further, the method includes determining, using the processing circuitry, whether the diaper change threshold is reached, and transmitting, via a network, a diaper change alert to an external device.

Further, according to an embodiment of the present disclosure, there is provided a non-transitory computer-readable medium which stores a program which, when executed by a computer, causes the computer to perform the diaper change alert method, as discussed above.

The forgoing general description of the illustrative implementations and the following detailed description thereof are merely exemplary aspects of the teachings of this disclosure, and are not restrictive.

BRIEF DESCRIPTION OF THE DRAWINGS

A more complete appreciation of the disclosed embodiments and many of the attendant advantages thereof will be readily obtained as the same becomes better understood by reference to the following detailed description when considered in connection with the accompanying drawings, wherein:

FIG. 4C illustrates a second screen of the DCA app according to an exemplary embodiment of the present disclosure.

FIG. 4D illustrates a third screen of the DCA app according to an exemplary embodiment of the present disclosure.

DETAILED DESCRIPTION

The description set forth below in connection with the appended drawings is intended as a description of various embodiments of the disclosed subject matter and is not necessarily intended to represent the only embodiment(s). In certain instances, the description includes specific details for the purpose of providing an understanding of the disclosed embodiment(s). However, it will be apparent to those skilled in the art that the disclosed embodiment(s) may be practiced without those specific details. In some instances, well-known structures and components may be shown in block diagram form in order to avoid obscuring the concepts of the disclosed subject matter.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "proximate," "minor," and similar terms generally refer to ranges that include the identified value within a margin of 20%, 10% or preferably 5% in certain embodiments, and any values therebetween.

Figure 1:
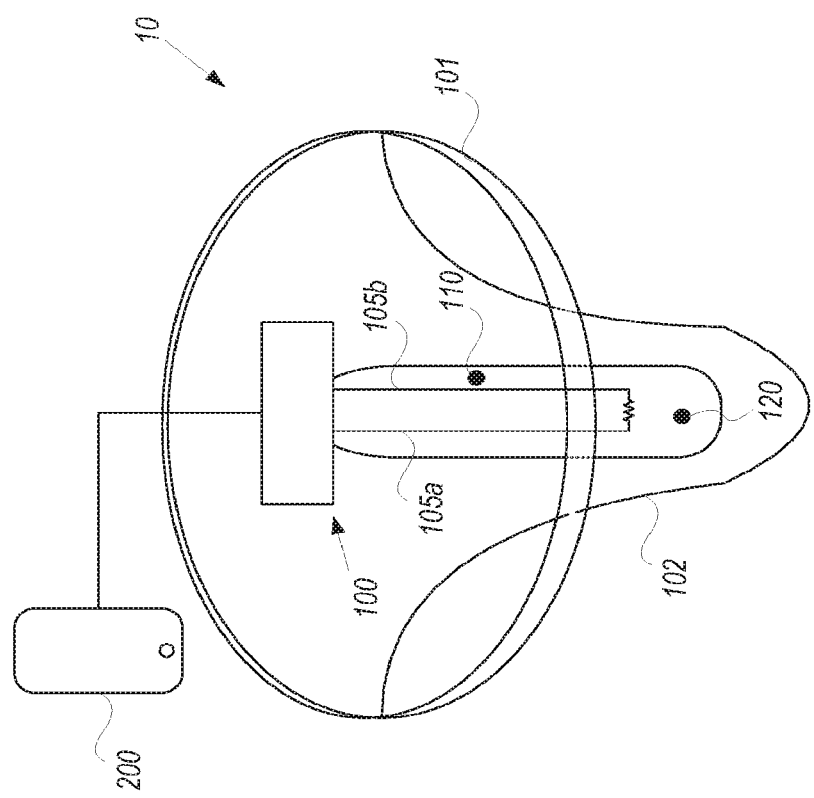
FIG. 1 is an exemplary diaper according to an exemplary embodiment of the present disclosure.

FIG. 1 is an exemplary diaper according to an exemplary embodiment of the present disclosure. A diaper 10 includes a strap 101, a wetness detection circuitry 100, a humidity sensor 110, and an ionic composition sensor 120 installed inside a seat portion 102. The wetness detection circuitry 100, the humidity sensor 110, and the ionic composition sensor 120 can send signal to a diaper change alert application (hereinafter referred as "DCA app") installed on a user device 200. The diaper 10 can be used for babies, adults, or animals.

In one embodiment of the present disclosure, the wetness detection circuitry 100 and the sensors 110 and 120 can be installed inside a detectable layer made of soft material similar to the diaper material. The detachable layer can be attached to a regular diaper to make the diaper 10. As such, the advantages and features of the present disclosure can be applied to a regular diaper as well.

The wetness detection circuitry 100 includes wires 105a and 105b (hereafter referred as 105) coupled to the wetness detection circuitry 100. In operation, the electrical resistance between the wires 105 falls when the wires 105 are contacted with urine or other wetness in the diaper. In turn, current is conducted through the wires 105 completing the electric circuit. As such, based on the current, wetness can be detected by the wetness detection circuitry 100. The wetness detection circuitry 100 can include a wireless transmitter and receiver to send and receive signals to the DCA app installed on the user device 200. In one embodiment, the wetness detection circuitry 100 can include one or more bulbs that glow upon completion of the electric circuit when urine or other liquid is discharged in the diaper. As such, the bulb can act as a visual indicator to change the diaper.

The humidity sensor 110 monitors a humidity level in the diaper. A high humidity level in the diaper 10 for an extended period of time can cause a rash. A time period for causing the rash can vary from person to person and changes in physical or medical information specific to a person. The time period can be measured in a total time per diaper change. Further, a correlation between the humidity level, a total time per diaper change, and a rash occurrence can be established based on past humidity level and rash data. Furthermore, a first rash threshold based on the humidity data can be established. For example, the first rash threshold can be 5 hours per diaper change, when the humidity level in the diaper s approximately 75%. The first ash thresholds can be updated manually as the physical or medical condition of the person changes via the DCA app.

The ionic composition sensor 120 can predict an amount of sodium, potassium, ammonium, calcium, magnesium, chloride, sulfate, phosphate, urate and creatinine in urine. The ionic composition of urine is a good indicator of a person's general health condition and allows for diagnostics of certain medical problems such as e.g., rash, malnutrition, infection, etc. The ionic composition can vary from person to person based on biological chemistry. Also, the ionic composition for the same person can vary based on dietary changes on a day-to-day basis. The ionic composition data collected over a period of time can be used to predict a rash occurrence. To enable such rash occurrence predictions, the ionic composition data can be correlated to a rash occurrence, and the total time per diaper change. The ionic composition a few days prior to the rash occurrence can be analyzed to establish the correlation. Furthermore, a second rash threshold can be established based on the ionic composition data. The second rash threshold can be a percentage of an element or a combination of elements of the ionic composition computed for the total time per diaper change. For example, the second threshold can be 70% chloride when the diaper 10 is changed every 5 hours, or the second thresholds can be a combination of elements such as 50% ammonia, 60% chloride, and 20% sulfate when the diaper 10 is changed every 5 hours. As such, the second threshold can account for the changes in physical or medical condition of the person wearing the diaper 10.

In one embodiment, other types of sensors can be installed such as a temperature sensor to measure the temperature inside the diaper 10, one or more pressure sensors to detect the position of a person wearing the diaper 10, or physiological sensors to monitor the health of the person wearing the diaper 10.

The DCA app is a software application installed on the user device 200. The functions of the DCA app include, but are not limited, to collecting waste information, diaper change information, rash information, and transmitting alerts to indicate diaper change is required. The DCA app functions are discussed in more detail with respect to FIGS. 2, 3, 4A, 4B, 4C, and 5. The DCA app includes an interface with several screens to enter information related to different aspects of the diaper change.

Figure 2:
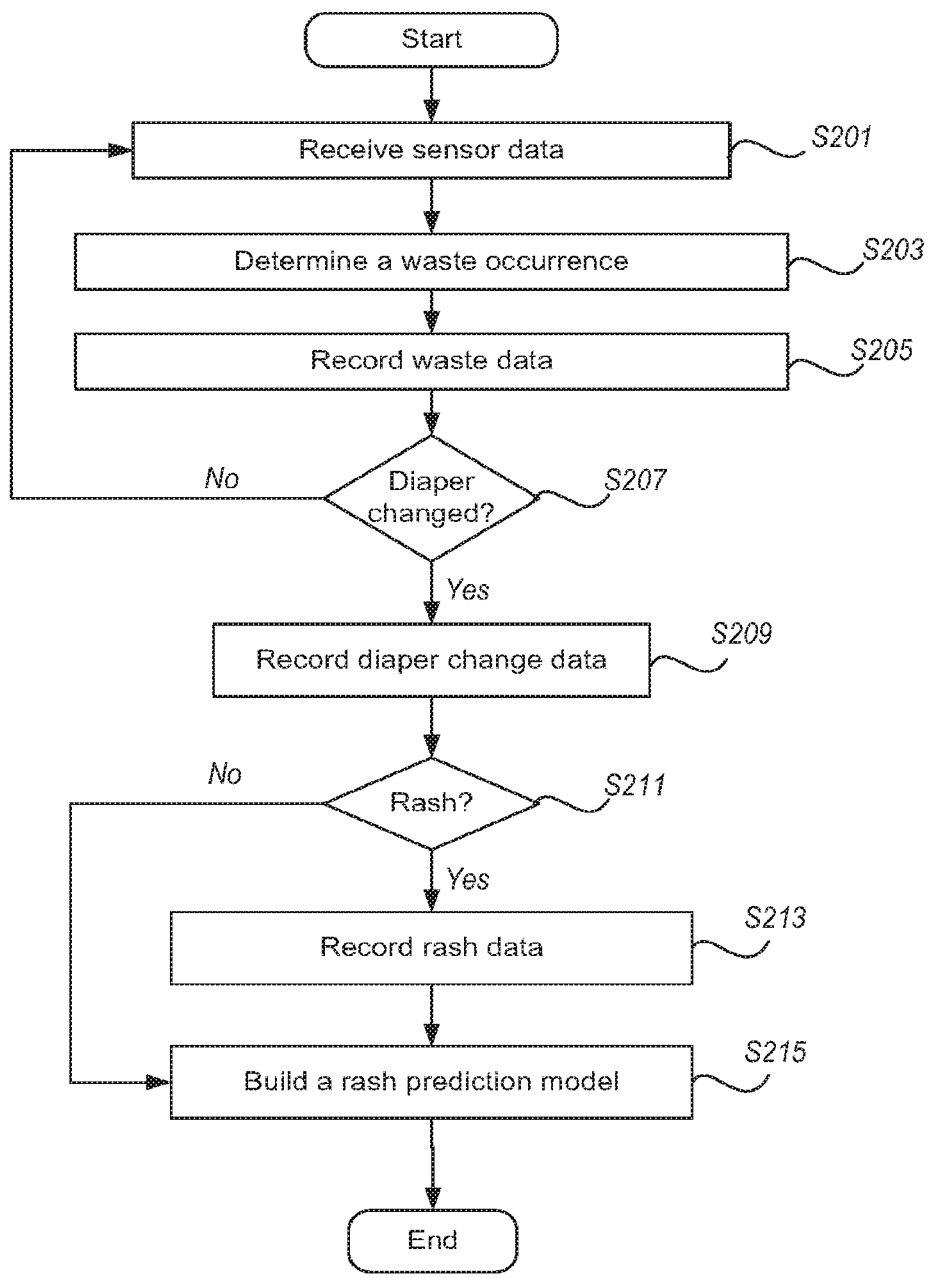
FIG. 2 is flow chart illustrating a process of building a rash prediction model according to an exemplary embodiment of the present disclosure.

FIG. 2 is flow chart illustrating a process of building a rash prediction model according to an exemplary embodiment of the present disclosure. The process starts when the diaper 10 is put on the person. In step S201, the DCA app installed on the user device 200 receives sensor data and signal from the wetness detection circuitry 100.

In step S203, the DCA app determines a waste occurrence based on the sensor data (e.g., data from sensors 110 and 120 and/or the wetness detection circuitry 100). The waste can be solids or liquid waste such as urine and feces.

In step S205, the waste related data is recorded in a memory of the user device 200. The data can be data received from the sensors 110 and 120 or other sensors installed in the diaper 10. In addition, the DCA app can be used to enter the waste related data using a first screen 400A (in FIG. 4B) of the DCA app.

In step S207, the DCA app determines whether the diaper 10 was changed. The diaper change can be determined based on the sensor data. When the diaper 10 is removed from the person, the sensor data will not be received indicating a diaper change is taking place. Alternatively or in addition, the diaper change can be detected when a user pushes a diaper change button 402 on home screen 400 (FIG. 4A) of the DCA app. In addition, a second screen 400B (in FIG. 4C) can be used to enter diaper change data. If the diaper is not changed, the process iteratively performs the steps S201, S203 and S205. When the diaper change is detected, the diaper change data can be recorded using the second screen 400B of the DCA app, in step S209.

In step S211, a determination is made whether a rash was observed. The rash occurrence can be visually detected by a user and when the user pushes a rash button 403 on the home screen 400 of the DCA app the rash is said to be detected. If a rash is detected, the user can enter rash related data in a third screen 400C (in FIG. 4C), in step S213. If no rash is observed, no rash information can be collected, but using the third screen 400C, a picture of the skin covered by the diaper can be taken and stored in the memory 550 of the user device 200.

In step S215, a rash prediction model is build based on the recorded data, as discussed above. One or more rash prediction model can be build using the recorded data. For example, a first rash prediction model based on humidity related data, a second rash model based on the ionic composition related data, a third rash prediction model based on the rash data, and a fourth rash prediction model based on a picture of a skin portion (covered by the diaper), humidity level, ionic composition, and a rash occurrence can be established.

Prior to building the first rash model, a first database can be created by relating the rash occurrence to the humidity level collected, while the diaper is on; a change in the humidity level with respect to time, while the diaper is on; and the time per diaper change. After creating the first database and collecting enough data points over a period of time, the first rash prediction model can be build. The first rash prediction model can be a linear regression model, Bayesian based model, or other appropriate statistical model, where the parameters of the model are computed based on factors including the humidity level, the change in humidity level, and the time per diaper change.

Prior to building the second rash model, a second database can be created by relating the rash occurrence to each of the elements of the ionic composition, while the diaper is on; a change in each of the elements of the ionic composition with respect to time, while the diaper is on; and the time per diaper change. After creating the second database and collecting enough data points over a period of time, the second rash prediction model can be build. The second rash prediction model can be a linear regression model, Bayesian based model, or other appropriate statistical model, where the parameters of the model are computed based on factors including each of the elements of the ionic composition, the change in each element of the ionic composition, and the time per diaper change.

A third rash prediction model can be based on the factors related to the rash data collected using the third screen 400C in FIG. 4D. For example, the rash occurrence can be related to the time per diaper change, and number of waste cycles per diaper change. Furthermore, a third database, using the aforementioned data, can be created and stored in the memory 550 of the user device 200.

The third database can be used to build the third rash prediction model, when enough data is collected. The third rash prediction model can be a linear regression model, Bayesian based model, or other appropriate statistical model, where the parameters of the model are computed based on factors including the time per diaper change and the number of waste cycles.

According to one embodiment of the present disclosure, the picture of the skin portion (covered by the diaper) can be before putting on a new diaper. The picture of the skin portion can be stored in the memory 550 of the user device 200 can be used to monitor a skin condition and to determine any deterioration in the skin condition leading to a rash formation. The changes in the skin condition can be identified using an image processing software, which compares a current picture of the skin portion to past pictures of the skin portion, apply anomaly detection algorithms and identify any change in the skin condition.

Furthermore, using the pictures of the skin portion (covered by the diaper), a fourth database and a fourth rash prediction model can build. The fourth database can be created by correlating the picture of the skin portion with factors including a color of the skin portion, humidity level, ionic composition, changes in humidity level per diaper change, changes in the ionic composition per diaper change, a rash size, a rash color, time of diaper change, and the number of waste cycles per diaper change. Thus, the fourth rash prediction model can anticipate the rash occurrence based on one or a combination of the aforementioned factors.

The fourth rash prediction models can be linear regression model or Bayesian based model. The Bayesian based model can be particularly useful, since they allow updating of parameters of the model based on present data, thus accommodating any changes in the physical condition of the person, diaper change schedule, or other factors affecting the diaper change or rash occurrence.

Figure 3:
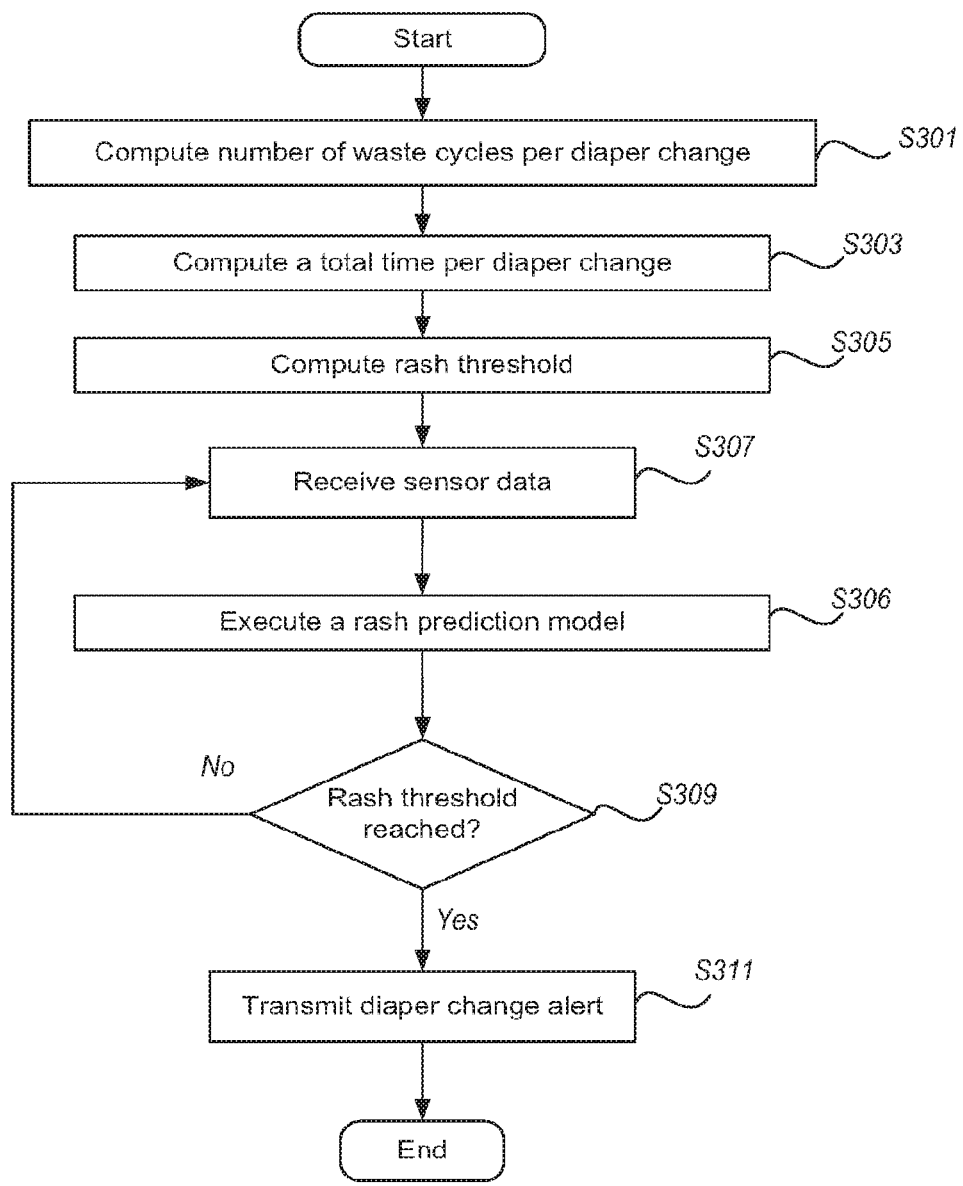
FIG. 3 is flow chart illustrating a rash prediction process according to an exemplary embodiment of the present disclosure.

FIG. 3 is flow chart illustrating a rash prediction process according to an exemplary embodiment of the present disclosure. The process starts when rash related data is collected by the DCA app. In step S301, the DCA app computes a number of waste cycles per diaper change. The number of waste cycle is number of times the person wearing the diaper 10 discharges bodily waste in the diaper before changing the diaper 10. The number of waste cycles can be determined based on the waste data stored in a memory 550 of the user device 200.

In step S303, the DCA app computes a total time per diaper change. The total time per diaper change can be determined based on the diaper change data stored in the memory 550 of the user device 200.

In step S305, the DCA app computes a rash threshold. The rash threshold can be a third rash threshold computed by correlating the rash data with the waste cycle per diaper change and the total time per diaper change. The third rash threshold can be measured in terms of the total time per diaper change, or number of waste cycles. For example, the third rash threshold can be 10 hours per diaper change, or 3 waste cycles per diaper change. The third rash threshold can also be computed using the rash property information collected using a third screen 400C (in FIG. 4D). The rash property can be a rash size, or a rash color. The rash property can be determined by visual inspection. Alternatively or in addition, the rash property can be determined by taking a rash picture using the third screen 400C, matching the rash picture with a plurality of rash pictures stored on a remote server (e.g., a server 600), and extracting the rash properties of the matching rash picture from the remote server. Then, the rash properties can be correlated with the total time per diaper change, the number of waste cycles per diaper change, the ionic composition of the waste, or the humidity level.

In addition, in step S305, the first rash threshold can be computed by correlating the humidity sensor data, as discussed earlier in the present disclosure. Furthermore, the second rash threshold can be computed by correlating the ionic composition data, as discussed earlier in the present disclosure. In one embodiment of the present disclosure, the first, second, and the third rash thresholds can be a probabilistic value that can be established using the data stored in the first, second, third, fourth databases, or a combination thereof. For example, the first rash threshold can be a 75% probability of getting a rash if the humidity level is 80% for more than 5 hours per diaper change. Similarly, a second, third, fourth etc. thresholds can be established.

In step S306, one or more rash prediction models, built in step S215 in FIG. 2, can be executed and the output can be compared to the rash thresholds, discussed in step S305. For example, the first rash prediction model can be executed to determine a first rash occurrence probability based on the humidity related data. Then, the first rash occurrence probability can then be compared to the first rash threshold. Similarly, the second rash prediction model can be executed to determine a second rash occurrence probability based on the ionic composition related data. The second rash occurrence probability can then be compared to the second rash threshold. A similar operation can be performed with the third rash prediction model and the fourth rash prediction model.

In step S307, the DCA app receives data from the sensors 110 and 120. The sensor data such as the humidity level and the ionic composition can used to compute a numeric value corresponding to the first and the second rash threshold, as discussed earlier with respect to FIG. 1. The numeric value can be measured in a similar manner as the first, second or third rash threshold. For example, the numeric value can be the time per diaper change, the ionic composition of sodium or a combination of elements such as chloride and sodium, etc.

In step S309, the DCA app determines if the rash threshold is reached. The DCA app can check the first rash threshold, the second rash threshold, and the third rash threshold simultaneously. If the first rash threshold, the second rash threshold, or the third rash threshold is not reached, the DCA app iteratively executes steps S301, S303, S305, and S307.

If any one of the first rash threshold, the second rash threshold, or the third rash threshold is reached, a diaper change alert is transmitted in step S311 to a user device. Furthermore, the diaper change alert can be transmitted based on the changes in the skin condition and the rash occurrence probability predicted by the fourth rash prediction model. For example, if the skin portion is darker than observed in past pictures, or a change in texture is identified on certain parts of the skin portion, the fourth prediction model can predict a time at which the rash will occur if the factors such as the humidity level, and/or the ionic composition remain approximately constant or increases over a certain period of time. Also, the first, second, third rash prediction models can be modified to set up an alert indicating an estimated time of rash occurrence. For example, a care taker can step up a time-based alert, such as send an alert 1 hour in advance of the estimated time of rash occurrence. Such alerts will allow user to assign a high priority to the diaper change task before the rash occurs.

The diaper change alert can be transmitted to one or more user devices. For example, a parent's user device, a nanny's user device, or a day care provider's user device. The DCA app can also allow the user to generate diaper change report regularly. The report can be used to analyze whether the nanny or the day care provider is doing a good job by regularly changing the diaper. Furthermore, the DCA app can compare the diaper change report from different nannies and day care provider that will allow parents, for example, to determine a good nanny or day care provider while making the hiring decision.

Figures 4A, 4B:
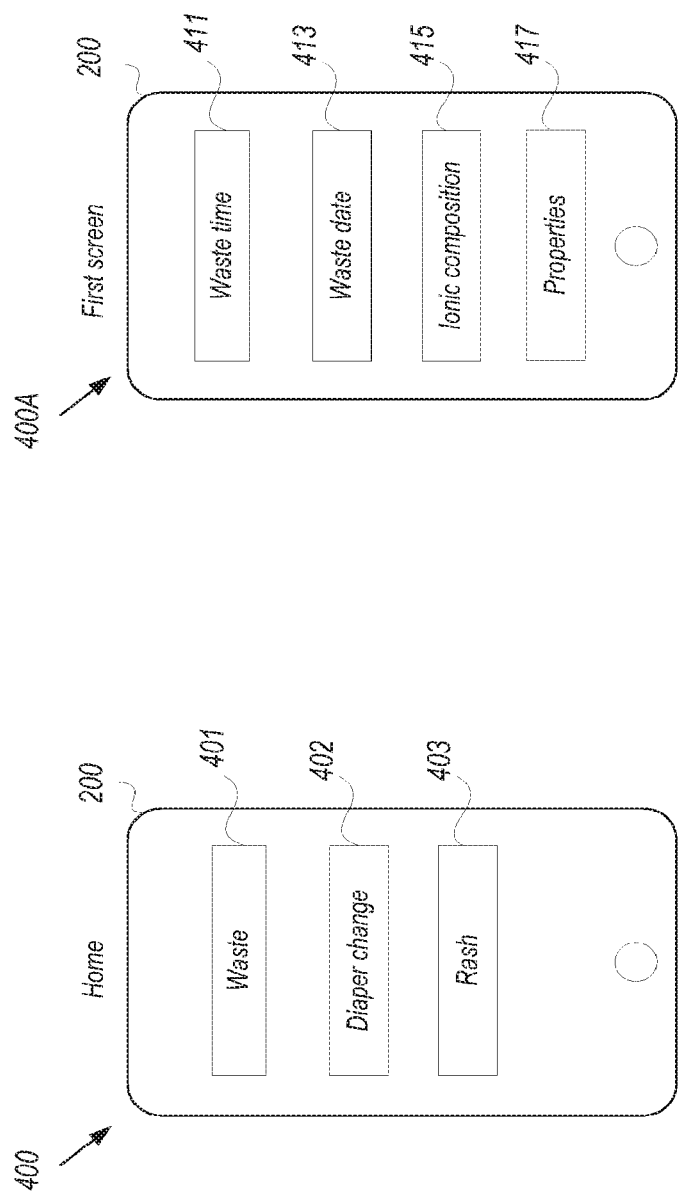
FIG. 4A illustrates a home screen of a diaper change alert application (DCA app) according to an exemplary embodiment of the present disclosure.
FIG. 4B illustrates a first screen of the DCA app according to an exemplary embodiment of the present disclosure.

FIG. 4A illustrates a home screen of the DCA app according to an exemplary embodiment of the present disclosure. The home screen 400 appears as part of the interface of the DCA app executed on the user device 200 when the DCA app is opened. The home screen 400 includes a waste button 401, a diaper change button 402, and a rash button 403. When the waste button 401 is activated, the first screen 400A is opened on the user device 200. When the diaper change button 402 is activated, the second screen 400B is opened on the user device 200. When the rash button 401 is activated, the third screen 400C is opened on the user device 200.

FIG. 4B illustrates the first screen 400A of the DCA app according to an exemplary embodiment of the present disclosure. The first screen 400A includes a waste time button 411, a waste date button 413, an ionic composition button 415, and a properties button 417. The waste time button 411 and the waste date 413 allow the user to input a time and date of the waste occurrence. The time and date can also be automatically populated based on data received from the sensors 110 and 120, or the wetness detection circuit 100. The ionic composition button 415, when activated, receives ionic composition data from the ionic composition sensor 120. Furthermore, the first screen 400A allows user to enter additional properties of the waste such as form, color, etc. using the properties button 417.

FIG. 4C illustrates the second screen 400B of the DCA app according to an exemplary embodiment of the present disclosure. The second screen 400B allows user to input information related to diaper change (DC). The second screen 400B includes a DC time button 421, a DC date button 423, and a DC number button 425. The DC time button 421 and the DC date 423 allow the user to input a time and date of the diaper change. The time and date can also be automatically populated based on data received (or not received diaper as is being changed) from the sensors 110 and 120, or the wetness detection circuit 100. Furthermore, the user can enter a number of times the diaper is being changed for the day using the DC number button 425.

FIG. 4D illustrates the third screen 400C of the DCA app according to an exemplary embodiment of the present disclosure. The third screen 400C includes a rash time button 431, a rash date button 433, a rash properties button 435, and a rash pic button 437. The rash time button 431 and the rash date 433 allow the user to input a time and date of the rash occurrence. The user can visually inspect the rash to confirm the occurrence of the rash. Alternatively or in addition, the user can take a picture of the rash using the rash pic button 437. The rash picture can be further compared and matched with a plurality of rash pictures in a memory, on a web site, or stored on the remote server to determine or confirm a type of rash. The remote server, or a memory of the user device 200 can include a database of rash types, rash picture per rash type and properties related to each rash type. Further, based on the matching rash, the properties of the matching rash can be automatically populated or displayed on a screen of the user device 200. Alternatively or in addition, the user may enter the rash properties such as size, color, texture, etc. by activating the rash properties button 435.

Each of the functions of the described embodiments may be implemented by one or more processing circuits or controller. A processing circuit includes a programmed processor (for example, controller 510), as a processor includes circuitry. A processing circuit may also include devices such as an application specific integrated circuit (ASIC) and conventional circuit components arranged to perform the recited functions. The processing circuit can be a part of the user device 200 as discussed in more detail with respect to FIG. 5.

Figure 5:
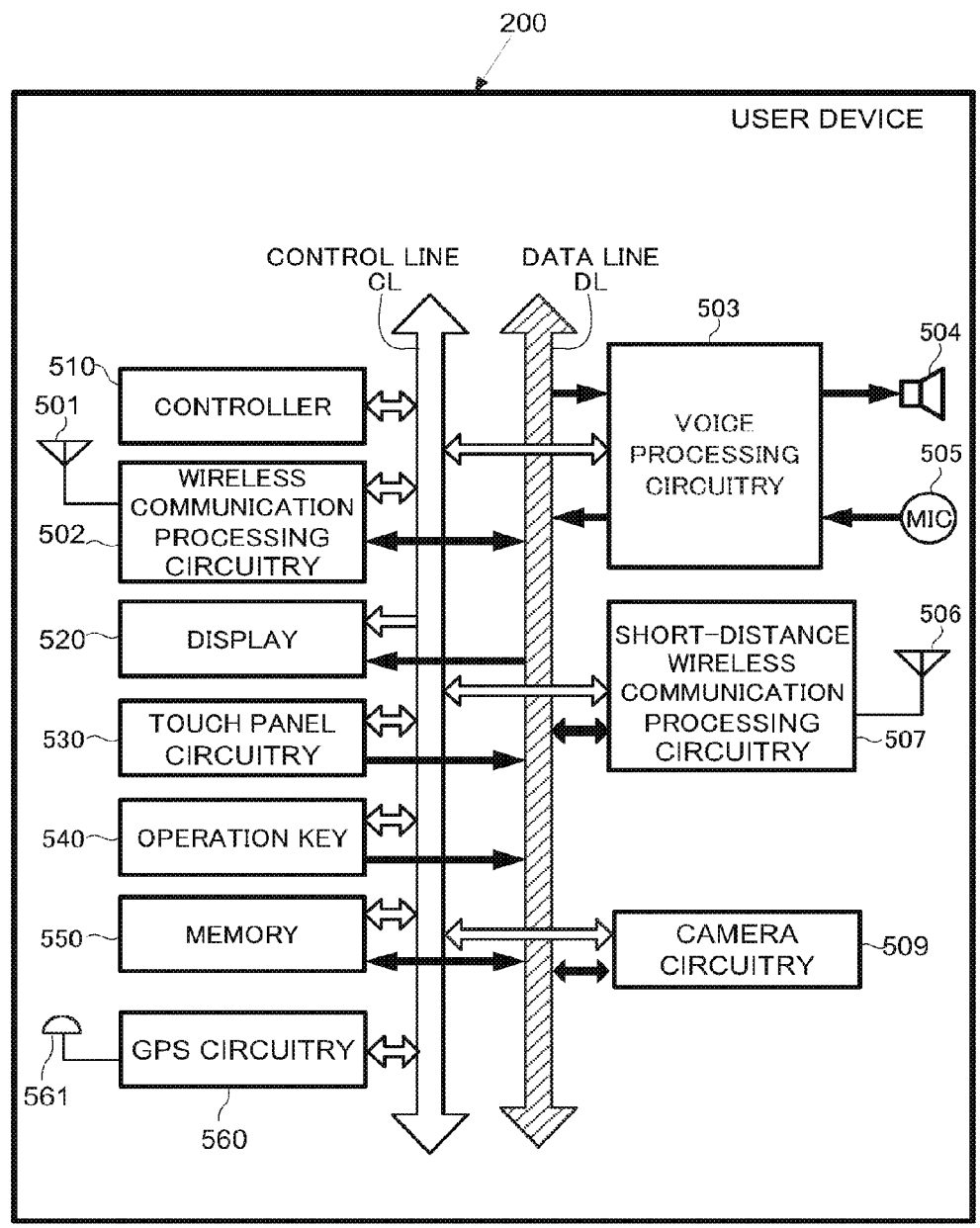
FIG. 5 is a detailed block diagram illustrating an exemplary user device according to certain embodiments of the present disclosure.

FIG. 5 is a detailed block diagram illustrating an exemplary user device 200 according to certain embodiments of the present disclosure. In certain embodiments, the user device 200 may be a smartphone. However, the skilled artisan will appreciate that the features described herein may be adapted to be implemented on other devices (e.g., a laptop, a tablet, etc.). The exemplary user device 200 includes a controller 510 and a wireless communication processing circuitry 502 connected to an antenna 501. A speaker 504 and a microphone 505 are connected to a voice processing circuitry 503.

The controller 510 is an example of the DCA app controller discussed with respect to FIGS. 2, 3, and 4A-4D and may include one or more Central Processing Units (CPUs), and may control each element in the user device 200 to perform functions related to communication control, audio signal processing, control for the audio signal processing, still and moving image processing and control, and other kinds of signal processing. The controller 510 may perform these functions by executing instructions stored in the memory 550. For example, the processes illustrated in FIGS. 2, 3, and 4A-4D may be stored in the memory 550 and executed based on the user inputs received via an interface such as 400 and 400A-400B. Alternatively or in addition to the local storage of the memory 550, the functions may be executed using instructions stored on an external device such as the server 600 accessed on a network or on a non-transitory computer readable medium.

The memory 550 includes but is not limited to Read Only Memory (ROM), Random Access Memory (RAM), or a memory array including a combination of volatile and non-volatile memory units. The memory 550 may be utilized as working memory by the controller 510 while executing the processes and algorithms of the present disclosure. Additionally, the memory 550 may be used for long-term storage, e.g., of image data and information related thereto. The memory 550 may be configured to store the battle view information, operation view information and list of commands.

The user device 200 includes a control line CL and data line DL as internal communication bus lines. Control data to/from the controller 510 may be transmitted through the control line CL. The data line DL may be used for transmission of voice data, display data, etc.

The antenna 501 transmits/receives electromagnetic wave signals between base stations for performing radio-based communication, such as the various forms of cellular telephone communication. The wireless communication processing circuitry 502 controls the communication performed between the user device 200 and other external devices such as a server or the wetness detection circuitry 100 via the antenna 501. The wireless communication processing circuitry 502 may control communication between base stations for cellular phone communication.

The speaker 504 emits an audio signal corresponding to audio data supplied from the voice processing circuitry 503. The microphone 505 detects surrounding audio and converts the detected audio into an audio signal. The audio signal may then be output to the voice processing circuitry 503 for further processing. The voice processing circuitry 503 demodulates and/or decodes the audio data read from the memory 550 or audio data received by the wireless communication processing circuitry 502 and/or a short-distance wireless communication processing circuitry 507. Additionally, the voice processing circuitry 503 may decode audio signals obtained by the microphone 505.

The exemplary user device 200 may also include a display 520, a touch panel 530, an operation key 540, and a short-distance communication processing circuitry 507 connected to an antenna 506. The display 520 may be a Liquid Crystal Display (LCD), an organic electroluminescence display panel, or another display screen technology. In addition to displaying still and moving image data, the display 520 may display operational inputs. For example, the operation inputs can be the waste button 401, the diaper change button 402, the rash button 403, the waste time button 411, the waste date button 413, the ionic composition button 415, the properties button 417, the DC time button 421, the DC date button 423, the DC number button 425, the rash time button 431, the rash date button 433, the rash properties button 435, and the rash pic button 437. The rash pic button 437 can activate a camera circuitry 509. The display 520 may additionally display a GUI having multiple screens as shown in FIG. 4A-4D, for a user to control aspects of the user device 200 and/or other devices. Further, the display 520 may display characters and images received by the user device 200 and/or stored in the memory 550 or accessed from an external device on a network such as a camera. For example, the user device 200 may access a network such as the Internet and display text and/or images transmitted from a Web server.

The touch panel 530 may include a physical touch panel display screen and a touch panel driver. The touch panel 530 may include one or more touch sensors for detecting an input operation on an operation surface of the touch panel display screen. The touch panel 530 also detects a touch shape and a touch area. Used herein, the phrase "touch operation" refers to an input operation performed by touching an operation surface of the touch panel display with an instruction object, such as a finger, thumb, or stylus-type instrument. In the case where a stylus or the like is used in a touch operation, the stylus may include a conductive material at least at the tip of the stylus such that the sensors included in the touch panel 530 may detect when the stylus approaches/contacts the operation surface of the touch panel display (similar to the case in which a finger is used for the touch operation).

In certain aspects of the present disclosure, the touch panel 530 may be disposed adjacent to the display 520 (e.g., laminated) or may be formed integrally with the display 520. For simplicity, the present disclosure assumes the touch panel 530 is formed integrally with the display 520 and therefore, examples discussed herein may describe touch operations being performed on the surface of the display 520 rather than the touch panel 530. However, the skilled artisan will appreciate that this is not limiting.

For simplicity, the present disclosure assumes the touch panel 530 is a capacitance-type touch panel technology. However, it should be appreciated that aspects of the present disclosure may easily be applied to other touch panel types (e.g., resistance-type touch panels) with alternate structures. In certain aspects of the present disclosure, the touch panel 530 may include transparent electrode touch sensors arranged in the X-Y direction on the surface of transparent sensor glass.

The touch panel driver may be included in the touch panel 530 for control processing related to the touch panel 530, such as scanning control. For example, the touch panel driver may scan each sensor in an electrostatic capacitance transparent electrode pattern in the X-direction and Y-direction and detect the electrostatic capacitance value of each sensor to determine when a touch operation is performed. The touch panel driver may output a coordinate and corresponding electrostatic capacitance value for each sensor. The touch panel driver may also output a sensor identifier that may be mapped to a coordinate on the touch panel display screen. Additionally, the touch panel driver and touch panel sensors may detect when an instruction object, such as a finger is within a predetermined distance from an operation surface of the touch panel display screen. That is, the instruction object does not necessarily need to directly contact the operation surface of the touch panel display screen for touch sensors to detect the instruction object and perform processing described herein. For example, in certain embodiments, the touch panel 530 may detect a position of a user's finger around an edge of the display panel 520 (e.g., gripping a protective case that surrounds the display/touch panel). Signals may be transmitted by the touch panel driver, e.g. in response to a detection of a touch operation, in response to a query from another element based on timed data exchange, etc.

The touch panel 530 and the display 520 may be surrounded by a protective casing, which may also enclose the other elements included in the user device 200. In certain embodiments, a position of the user's fingers on the protective casing (but not directly on the surface of the display 520) may be detected by the touch panel 530 sensors. Accordingly, the controller 510 may perform display control processing described herein based on the detected position of the user's fingers gripping the casing. For example, an element in an interface may be moved to a new location within the interface (e.g., closer to one or more of the fingers) based on the detected finger position.

Further, in certain embodiments, the controller 510 may be configured to detect which hand is holding the user device 200, based on the detected finger position. For example, the touch panel 530 sensors may detect a plurality of fingers on the left side of the user device 200 (e.g., on an edge of the display 520 or on the protective casing), and detect a single finger on the right side of the user device 200. In this exemplary scenario, the controller 510 may determine that the user is wearing the user device 200 with his/her right hand because the detected grip pattern corresponds to an expected pattern when the user device 200 is wearing only with the right hand.

The operation key 540 may include one or more buttons or similar external control elements, which may generate an operation signal based on a detected input by the user. In addition to outputs from the touch panel 530, these operation signals may be supplied to the controller 510 for performing related processing and control. In certain aspects of the present disclosure, the processing and/or functions associated with external buttons and the like may be performed by the controller 510 in response to an input operation on the touch panel 530 display screens rather than the external button, key, etc. In this way, external buttons on the user device 200 may be eliminated in lieu of performing inputs via touch operations, thereby improving water-tightness.

The antenna 506 may transmit/receive electromagnetic wave signals to/from other external apparatuses, and the short-distance wireless communication processing circuitry 507 may control the wireless communication performed between the other external apparatuses. Bluetooth, IEEE 802.11, and near-field communication (NFC) are non-limiting examples of wireless communication protocols that may be used for inter-device communication via the short-distance wireless communication processing circuitry 507.

The user device 200 may include the camera circuitry 509, which includes a lens and shutter for capturing photographs of the surroundings around the user device 200. In an embodiment, the camera circuitry 509 captures surroundings of an opposite side of the user device 200 from the user. The images of the captured photographs can be displayed on the display panel 520. A memory circuitry saves the captured photographs. The memory circuitry may reside within the camera circuitry 509 or it may be part of the memory 550. The camera circuitry 509 can be a separate feature attached to the user device 200 or it can be a built-in camera feature. Furthermore, the camera circuitry 509 can be configured to detect features of motion (i.e., one or more movements) of the user device 200 or user activities as discussed earlier with reference to FIG. 4D.

The DCA app implemented on the user device 200 is an application that can request data processing from a server 600. The server 600, in FIG. 6, includes a storage controller 624 that manages the database on a database 604 and a query manager app that executes SQL (structured query language) statements against this data on the database 604. The query manager app also implements processing functions (e.g. query syntax analysis, optimization, and execution plan generation) as well as a simple network communication function to send and receive signal from a network controller 606. A more detailed description of hardware of the server 600 is as follows.

Figure 6:
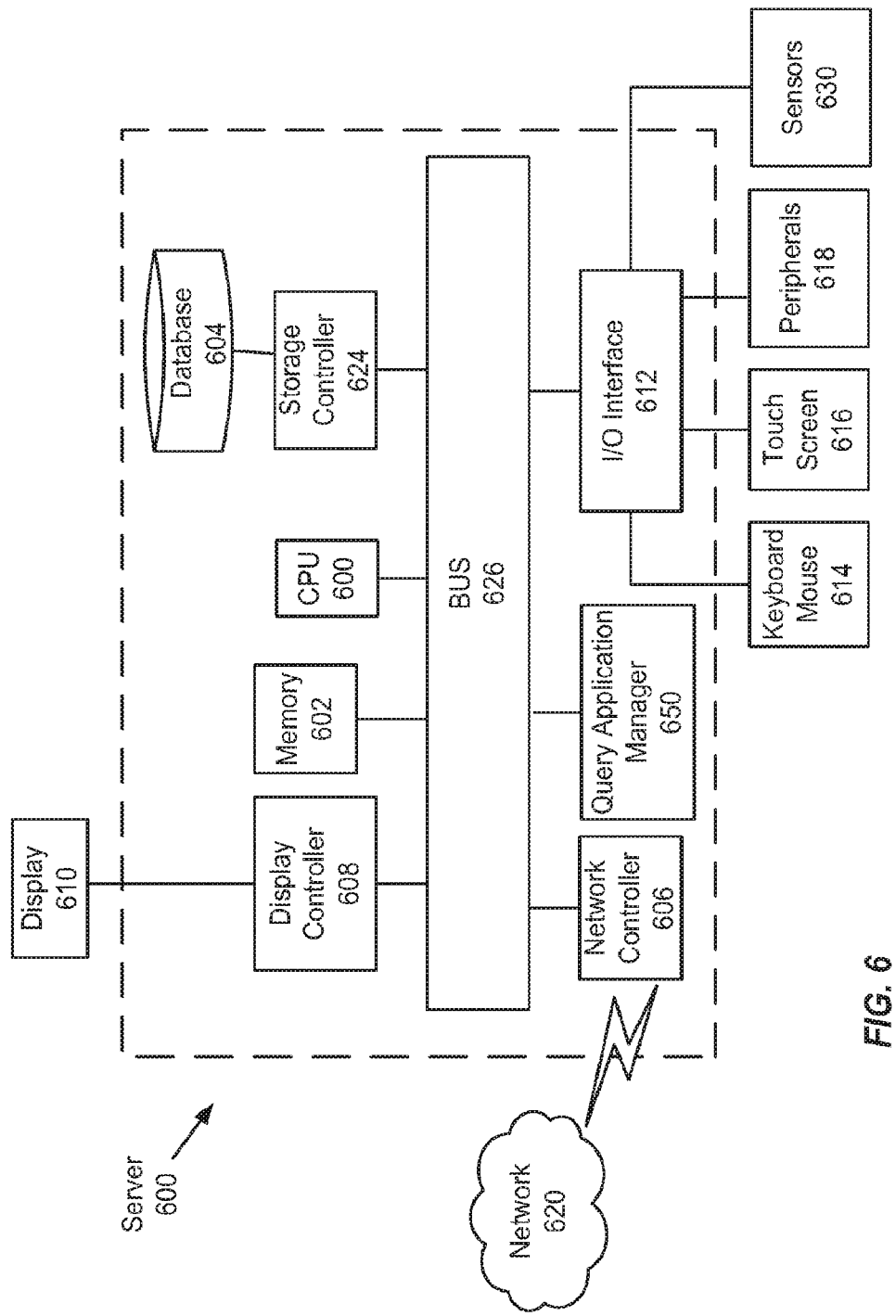
FIG. 6 is a detailed block diagram illustrating an exemplary server according to certain embodiments of the present disclosure.

FIG. 6 is a detailed block diagram illustrating an exemplary server 600 according to certain embodiments of the present disclosure. In FIG. 6, the server 600 includes a CPU 600 which performs the processes described in the present disclosure. The process data, instructions and rash related data such rash pictures, properties etc. may be stored in a memory 602. These processes, and instructions may also be stored on a storage medium database 604 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the server 600 communicates, such as a server or computer.

Further, the claimed advancements may be provided as a utility application, background daemon, or component of an operating system, or combination thereof, executing in conjunction with CPU 600 and an operating system such as Microsoft Windows 7, UNIX, Solaris, LINUX, Apple MAC-OS and other systems known to those skilled in the art.

The hardware elements in order to achieve the server 600 may be realized by various circuitry elements, known to those skilled in the art. For example, CPU 600 may be a Xenon or Core processor from Intel of America or an Opteron processor from AMD of America, or may be other processor types that would be recognized by one of ordinary skill in the art. Alternatively, the CPU 600 may be implemented on an FPGA, ASIC, PLD or using discrete logic circuits, as one of ordinary skill in the art would recognize. Further, CPU 600 may be implemented as multiple processors cooperatively working in parallel to perform the instructions of the inventive processes described above with respect to FIGS. 2, 3, and 4A-4D.

The server 600, in FIG. 6, also includes the network controller 606, such as an Intel Ethernet PRO network interface card from Intel Corporation of America, for interfacing with a network 620. As can be appreciated, the network 620 can be a public network, such as the Internet, or a private network such as an LAN or WAN network, or any combination thereof and can also include PSTN or ISDN sub-networks. The network 620 can also be wired, such as an Ethernet network, or can be wireless such as a cellular network including EDGE, 3G and 6G wireless cellular systems. The wireless network can also be WiFi, Bluetooth, or any other wireless form of communication that is known. The server 600 can communicate with external devices such as the external device via the network controller 606.

The server 600 can further include a display controller 608, such as a NVIDIA GeForce GTX or Quadro graphics adaptor from NVIDIA Corporation of America for interfacing with display 610. The display 610 can be display of the external device. An I/O interface 612 interfaces with a keyboard and/or mouse 614 as well as a touch screen panel 616 on or separate from display 610. The I/O interface also connects to a variety of peripherals 618 including printers and scanners, such as an OfficeJet or DeskJet from Hewlett Packard. The I/O interface can also connect to a variety of sensors 630 as discussed with respect to FIG. 1. Sensors 630 can be exemplary representation of the humidity sensor 110 and the ionic composition sensor 120.

Further, the server 600 can be connected to the external device via I/O interface 612 or through the network 620. The external device can send queries that are handled by a query manager application 650 including extracting data from the database 604 via the storage controller 624, from the memory 602, or trigger execution of processes discussed in FIGS. 2, 3, and 4A-4D.

The storage controller 624 connects the storage medium database 604 with communication bus 626, which may be an ISA, EISA, VESA, PCI, or similar, for interconnecting all of the components of the server 600. A description of the general features and functionality of the display 610, keyboard and/or mouse 614, as well as the display controller 608, storage controller 624, network controller 606, and the I/O interface 612 is omitted herein for brevity as these features are known.

In the above description, any processes, descriptions or blocks in flowcharts should be understood as representing modules, segments or portions of code which include one or more executable instructions for implementing specific logical functions or steps in the process, and alternate implementations are included within the scope of the exemplary embodiments of the present advancements in which functions can be executed out of order from that shown or discussed, including substantially concurrently or in reverse order, depending upon the functionality involved, as would be understood by those skilled in the art. The various elements, features, and processes described herein may be used independently of one another, or may be combined in various ways. All possible combinations and subcombinations are intended to fall within the scope of this disclosure.

While certain embodiments have been described, these embodiments have been presented by way of example only, and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosure. The accompanying claims and their equivalents are intended to cover such forms or modifications as would fall within the scope and spirit of the present disclosure. For example, this technology may be structured for cloud computing whereby a single function is shared and processed in collaboration among a plurality of apparatuses via a network.

What is claimed is:

1. A diaper change alert system, the system comprising:
a diaper with wetness detection circuit installed inside a seat portion of the diaper;
an ionic composition sensor installed inside the seat portion of the diaper;
a humidity sensor installed inside of the seat portion of the diaper;
processing circuitry configured to
build one or more rash prediction models,
compute number of waste cycles per diaper change based on a signal received from the wetness detection circuit,
compute a total time per diaper change based on a signal received from the wetness detection circuit,
compute a rash threshold using rash information,
receive sensor data,
determine whether the rash threshold is reached using the one or more rash prediction models, and
transmit, via a network, a diaper change alert to an external device, when the rash threshold is reached.

2. The system according to claim 1, wherein the rash threshold is a first rash threshold determined using the humidity sensor data collected over a period of time.

3. The system according to claim 2, wherein the first rash threshold is determined by establishing a correlation between a humidity level and the total time per diaper change.

4. The system according to claim 1, wherein the rash threshold is a second rash threshold determined using the ionic composition sensor data collected over the total time per diaper change.

5. The system according to claim 4, wherein the second rash threshold is determined by establishing a correlation between the ionic composition at the time of or before the rash detection and the total time per diaper change.

6. The system according to claim 1, wherein the rash threshold is a third rash threshold determined based on rash information identified visually and input in the processing circuitry.

7. The system according to claim 6, wherein the rash information input in the processing circuitry is a rash property including a rash color, a rash size, and a rash texture.

8. The system according to claim 7, wherein the rash property is determined by taking a rash picture, matching the rash picture with a plurality of rash pictures stored on a remote server, and extracting properties of the matching rash picture from the remote server.

9. The system according to claim 8, wherein the third rash threshold is determined by establishing a correlation between the rash information, the number of waste cycles per diaper change, and the total time per diaper change.

10. A diaper change alert method, comprising:
   computing, using processing circuitry, a number of waste cycles per diaper change;
   computing, using the processing circuitry, a total time per diaper change;
   computing, using the processing circuitry, a rash threshold using rash information;
   receiving, using the processing circuitry, sensor data;
   determining, using the processing circuitry, whether the rash threshold is reached using a rash prediction model; and
   transmitting, via a network, a diaper change alert to an external device when the rash threshold is reached.

11. The method according to claim 10, wherein the rash threshold is a first rash threshold determined using the humidity sensor data collected over a period of time.

12. The method according to claim 11, wherein the first rash threshold is determined by establishing a correlation between a humidity level and the total time per diaper change.

13. The method according to claim 10, wherein the rash threshold is a second rash threshold determined using the ionic composition sensor data collected over the total time per diaper change.

14. The method according to claim 13, wherein the second rash threshold is determined by establishing a correlation between the ionic composition at the time of or before the rash detection and the total time per diaper change.

15. The method according to claim 10, wherein the rash threshold is a third rash threshold determined based on rash information identified visually and input in the processing circuitry.

16. The method according to claim 15, wherein the rash information input in the processing circuitry includes a rash property.

17. The method according to claim 16, wherein the rash property is at least one of
   a rash color, and
   a rash size.

18. The method according to claim 16, wherein the rash property is determined by taking a rash picture, matching the rash picture with a plurality of rash pictures stored on a remote server, and extracting properties of the matching rash picture from the remote server.

19. The method according to claim 18, wherein the third rash threshold is determined by establishing a correlation between the rash information, the number of waste cycles per diaper change, and the total time per diaper change.

20. A non-transitory computer-readable medium storing a program which when executed by a computer, causes the computer to perform a method for diaper change alert, the method comprising:
   computing a number of waste cycles before a diaper change;
   computing a total time before each diaper change;
   computing a rash threshold using rash information;
   receiving sensor data;
   determining whether the rash threshold is reached using a rash prediction model; and
   transmitting, via a network, a diaper change alert to an external device when the rash threshold is reached.

* * * * *